US008545820B2

(12) United States Patent
Hobbs et al.

(10) Patent No.: US 8,545,820 B2
(45) Date of Patent: Oct. 1, 2013

(54) USE OF TITANIUM-BASED MATERIALS AS BACTERICIDES

(75) Inventors: David T. Hobbs, North Augusta, SC (US); Mark C. Elvington, Aiken, SC (US); John Wataha, Edmonds, WA (US); Whasun O. Chung, Lake Forest Park, WA (US); R. Bruce Rutherford, Seattle, WA (US); Daniel C. Chan, Seattle, WA (US)

(73) Assignees: Savannah River Nuclear Solutions, LLC, Aiken, SC (US); University of Washington Center for Commercialization, Seattle, WA (US)

( * ) Notice: Subject to any disclaimer, the term of this patent is extended or adjusted under 35 U.S.C. 154(b) by 0 days.

(21) Appl. No.: 13/135,745

(22) Filed: Jul. 14, 2011

(65) Prior Publication Data

US 2012/0156145 A1 Jun. 21, 2012

Related U.S. Application Data

(60) Provisional application No. 61/364,200, filed on Jul. 14, 2010.

(51) Int. Cl.

| | |
|---|---|
| ***A61K 8/29*** | (2006.01) |
| ***A61K 33/24*** | (2006.01) |
| ***A61Q 11/00*** | (2006.01) |

(52) U.S. Cl.

USPC .............. 424/49; 424/646; 424/649; 423/598

(58) Field of Classification Search

USPC ............................ 423/598; 424/646, 649, 49

See application file for complete search history.

(56) References Cited

U.S. PATENT DOCUMENTS

| | | | | |
|---|---|---|---|---|
| 4,229,430 | A * | 10/1980 | Fahim et al. | 424/49 |
| 5,688,492 | A * | 11/1997 | Galley et al. | 424/49 |
| 7,494,640 | B1 | 2/2009 | Niman et al. | |
| 2008/0142448 | A1 | 6/2008 | Hobbs et al. | |
| 2008/0145450 | A1 | 6/2008 | Hobbs et al. | |

OTHER PUBLICATIONS

Hobbs et al., “Absorption of Biometals to Monosodium Titanate in Biological Environments”, Journal of Biomedical Materials Research Part B: Applied Biomaterials, vol. 78B, Issue 2, pp. 296-301, Aug. 2006.*

American Chemical Society, Nyman and Hobbs “A Family of Peroxo-Titanate Materials Tailored for Optimal Strontium and Actinide Sorption” Chem. Matter, Published on Web Nov. 18, 2006, 18 (26), p. 6425-6435 (11Pages).

The Journal of Biomedical Materials Reasearch, Chung et al.; “Peroxotitanate-and Monosodium Metal-Type Tinate Compound As Inhibitors of Bacterial Growth”, Jun. 2011 vol. 97A, Issue 3, pp. 348-354.

* cited by examiner

*Primary Examiner* — Lezah Roberts

(74) *Attorney, Agent, or Firm* — J. Bennett Mullinax, LLC

(57) ABSTRACT

Compositions containing metal ions bound into a titanate are described which have demonstrated an ability to suppress bacterial growth of a number of organisms associated with periodontal disease and caries.

7 Claims, 2 Drawing Sheets

USE OF TITANIUM-BASED MATERIALS AS BACTERICIDES

RELATED APPLICATIONS

This application claims the benefit of US Provisional Application, having Ser. No. 61/364,200, filed on Jul. 14, 2010 and entitled "Use of Titanium-Based Materials as Bactericide" and which is incorporated herein by reference.

STATEMENT AS TO RIGHTS TO INVENTIONS MADE UNDER FEDERALLY SPONSORED RESEARCH AND DEVELOPMENT

This invention was made with Government support under Contract No. DE-AC09-08SR22470 awarded by the United States Department of Energy. The Government has certain rights in the invention.

FIELD OF THE INVENTION

This invention is directed towards the use of metal ions delivered from a solid phase material to suppress the growth of bacteria.

BACKGROUND OF THE INVENTION

The metal ion suppression of bacterial growth is well known. However, levels of the anti-bacterial metal ions required to achieve a therapeutic reduction in bacteria growth are typically at a level that will produce undesirable side effects in mammals.

The use of metal ions to control bacterial infections remains of interest as drug-resistant bacteria are becoming increasingly common and dangerous to human health. Accordingly, there remains room for variation and improvement within the art directed to metal ion suppression of bacterial growth.

SUMMARY OF THE INVENTION

It is one aspect of at least one of the present embodiments to provide for metal ions which are complexed to titanates and peroxotitanates. Such a combination has been found to reduce the amount of metal ions needed to suppress bacterial growth.

It is another aspect of at least one of the present embodiments of the invention to provide a synergistic delivery platform to provide metal ions that suppress the growth of bacterial cells wherein the therapeutics affects are achieved at metal ion concentrations having a least one order of magnitude less than metal ion concentrations absent the delivery platform.

It is a further aspect of at least one of the present embodiments of the invention to provide for a delivery platform comprising amorphous peroxotitanate (APT) and monosodium titanate (MST) which are loaded with at least one of the metal ion selected from the group of Au(III), Pt(IV), Pt(II) and Pd(II) in which the APT/MST metal ion loaded particles have an ability to synergistically increase the effectiveness of the metal ions in terms of suppression of bacteria growth in comparison to applicable controls of metal ions alone or the carrier platform of APT or MST alone.

It is a further aspect of at least one embodiment of the present invention to provide an effective delivery system of metal ions having anti-bacterial properties that are suitable for treating bacterial associated periodontal disease.

It is a further aspect of at least one embodiment of the present invention to provide an effective delivery system of metal ions having anti-bacterial properties that are suitable for reducing the frequency or progression of caries.

A further aspect of at least one embodiment of the present invention is to provide a sustained-release oral ointment or paste which comprises a carrier ointment, an adhesive substance, and an anti-microbial metal ion which is attached to APT or MST.

A further aspect of at least one embodiment of the present invention is to provide for an oral ointment in the form of a medicine, an injectable fluid, toothpaste, oral gel, paste, a denture cream, or an oral rinse which can deliver to a periodontal pocket, or a carious lesion, a therapeutic amount of a metal ion complexed with either APT or MST.

These and other features, aspects, and advantages of the present invention will become better understood with reference to the following description and appended claims.

BRIEF DESCRIPTION OF THE DRAWINGS

A fully enabling disclosure of the present invention, including the best mode thereof to one of ordinary skill in the art, is set forth more particularly in the remainder of the specification, including reference to the accompanying drawings.

DESCRIPTION OF THE PREFERRED EMBODIMENT

Figure 1:
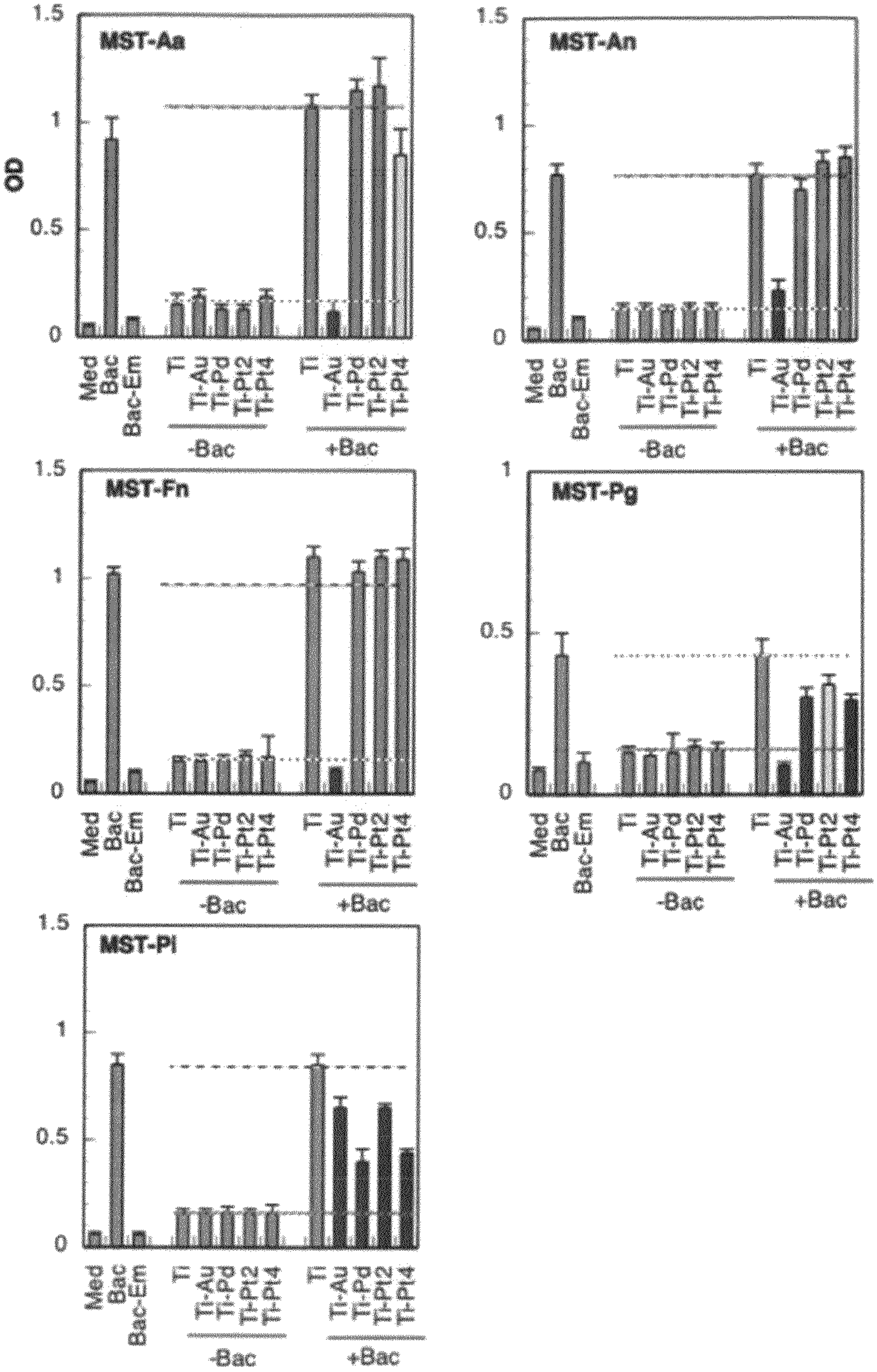
FIG. 1 are dose response curves setting forth the effect of MST loaded with various metals and the effect of the growth rate of the bacteria listed in Table 2.

Reference will now be made in detail to the embodiments of the invention, one or more examples of which are set forth below. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used on another embodiment to yield a still further embodiment. Thus, it is intended that the present invention cover such modifications and variations as come within the scope of the appended claims and their equivalents. Other objects, features, and aspects of the present invention are disclosed in the following detailed description. It is to be understood by one of ordinary skill in the art that the present discussion is a description of exemplary embodiments only and is not intended as limiting the broader aspects of the present invention, which broader aspects are embodied in the exemplary constructions.

The formation of MST and an APT are known in the art from the use of such materials for sorbents of radionuclides. Various types of synthesis routes and characterization of MST and APT can be found in reference to the following publications. American Chemical Society, A Family of Peroxo-titanate Materials Tailored for Optimal Strontium and Actinide Sorption Chem. Mater., 2006, 18 (26), page 6425-6435, and which is incorporated herein by reference. Additional background information with respect to titanate materials may be found in reference to U.S. Pat. No. 7,494,640, which is incorporated herein by reference and U.S. patent application Ser. No. 11/638,843 filed Dec. 14, 2006, and which is incorporated herein by reference.

Materials and Methods

The MST is available as an aqueous suspension at ph 11.7 having approximately 15 wt % solids from Optima Chemical Groups, Douglas, Ga. The pH of a stock MST suspension was adjusted to 7.4 using a reagent grade nitric acid (Fisher). A stock solution of MST of 3,000 mg/L was diluted in sterile distilled water to working concentration as set forth below.

APT was produced by treating MST with a solution of hydrogen peroxide. Excess hydrogen peroxide was removed by filtration. The isolated solids were washed with ionized distilled water and the APT solids were then suspended in water and adjusted to pH 4 with dilute nitric acid. In preparation of the metal-loaded APT materials as set forth below, a stock suspension of the APT was adjusted with NaOH solution to a pH of 7.4 and the solids content adjusted to 2000 mg/L.

Titanate (APT or MST) Loading with Metal Compounds

APT and MST particles were loaded with Au(III), Pt(IV), Pt(II) or Pd(II) by combining 0.25 g of titanate (APT or MST individually) suspended in 1.4 g of water (pH=6.9) with 10 mL of a phosphate-buffered saline solution containing the desired metal ion. To maximize metal loading to the particles, the concentrations of metals in the loading solutions were maximized (limited by solubility in PBS) to provide the greatest driving force to load metal onto the particles. After mixing at ambient temperature for 48 h, the metal-APT materials were separated from the parent solutions by centrifugation (RCF=1200×g, 3 min), after which the solid phases were rinsed quickly with 6 portions of chilled PBS (4° C.; pH=7.4), then stored as moist solids with water contents of approximately 75 wt %. Maintaining moist solids greatly increased the ability to re-suspend the particles in solution during bacteria-culture experiments.

The amount of metal compounds loaded onto the titanate was determined by measuring the difference in metal concentrations of the metal loading solutions before and after contact with the titanate solids. Metal ion concentrations in the solutions before and after contact with the solids were determined using inductively coupled plasma emission spectroscopy (ICP-ES) and inductively coupled plasma mass spectroscopy (ICP-MS) techniques. Metal loading was reported as the number of picomoles (picomol) of metal per μg of titanate. As used herein, the term "metal loading" is used to refer to any form of attachment of the metal to the respective titanate. Such forms of interaction may include sorption or some type of ligand interaction. If desired, ionic or covalent bonding can be used including the use of other chemical reagents that might bring about improved binding of the metal to the titanate. For instance, conjugation through the use of proteins bound to one or more of the metals and/or titanates may be used.

Bacterial Cultures

Set forth in Table 1 are the species of oral bacteria which were evaluated. These species are atiologic agents and periodontal disease, gingivitis, or caries that would lend themselves to treatment with a solid-phase metal titanate compound. *Porphyromonas gingivalis* (Pg) (American Type Culture Collection #33277) was cultured under anaerobic conditions (85% $N_2$, 10% $H_2$, 5% $CO_2$) at 37° C. in trypticase soy broth (BBL, Sparks Md.) supplemented with 1 g of yeast extract, 5 mg of hemin, and 1 mg of menadione per L. *Fusobacterium nucleatum* (Fn) (ATCC #43718) and *Agregatibacter actinomycetemcomitans* (Aa) (ATCC #25586) were cultured in Todd-Hewitt broth supplemented with 10 g of yeast extract/L at 37° C. under the same anaerobic conditions. *Streptococcus mutans* (Sm) (ATCC #700610) was cultured under aerobic conditions (100% room air) at 37° C. in trypticase soy broth. *Prevotella intermedia* (Pi) (ATCC #25611) was cultured under anaerobic conditions in trypticase soy broth supplemented with 0.5% yeast extract, 0.05% cysteine, 0.5 mg/mL hemin, and 2 μg/mL menadione, and *Actinomyces naeslundii* (An) (ATCC #19039) was cultured in an oxygen-depleted, $N_2$-free atmosphere at 37° C. in BBL *Actinomyces* broth. All bacteria were cultured from frozen stocks expanded from ATCC cultures; the absence of contamination was verified at each thaw via Gram stain. All bacteria were grown over 24 h to mid-log phase before inoculating experimental cultures.

TABLE 1

Bacteria evaluated

| Bacteria (Code) | Full Name | Source (ATCC*) | Gram Staining | Role in oral disease | Culture condition |
|---|---|---|---|---|---|
| Aa | *Aggregatibacter actinomycetemcomitans* | 25586 | negative | aggressive periodontal pathogen | anaerobic (85%$N_2$, 10%$H_2$, 5% $CO_2$) |
| An | *Actinomyces naeslundii* | 19039 | positive | root caries, early childhood caries | $N_2$-free, $O_2$ depleted |
| Fn | *Fusobacterium nucleatum* | 43718 | negative | bridging organism between pathogens and non-pathogens | anaerobic (85%$N_2$, 10%$H_2$, 5% $CO_2$) |
| Pg | *Porphyromonas gingivalis* | 33277 | negative | periodontal pathogen | anaerobic (85%$N_2$, 10%$H_2$, 5% $CO_2$) |
| Pi | *Prevotella intermedia* | 25611 | negative | gingival and periodontal pathogen | anaerobic (85%$N_2$. 10%$H_2$, 5% $CO_2$) |

*American Type Culture Collection number.

Exposure of Bacteria to Metal Ions, Titanates, and Metal-Titanium Compounds

One hundred μL of the initial culture was plated in 96 well plate format number of bacterial cells present in a given volume of culture was determined by correlating OD reading of bacterial culture at 595 nm to the number of cells present. This method is based on a previously established system of how OD reading converts to colony forming units for each bacterial species (Chung and Dale, 2008; Chung et al., 2010). Prior to exposing bacteria to metal-titanate compounds, appropriate dilutions of each bacterial species were made so that metal-titanate compounds are consistently exposed to 3.56E9 bacteria for all species tested. This strategy assured the same cell to titanate particle ratio, allowed repeatability, and allowed log growth phase throughout the 24 h time when bacteria were exposed to the titanates. A 24 h incubation time with titanates was chosen to maximize the exposure to the titanates without risking a culture deteriorating from overgrowth. Typical initial OD readings were 0.05; typical final OD readings were 0.4+.

For metal ions alone, 5 μL of a concentrated stock solution of the respective metal salt were added to 95 μL of the bacterial cultures (n=8 per condition). For MST and APT experiments, 5 μL/well of a stock titanate solution was added to provide a final titanate concentration of 0-25 μg/mL (n=8). The cultures were mixed to ensure contact between the titanates and the bacteria. MST and APT suspensions were thoroughly mixed prior to addition to ensure accurate transfer of the particles. Concentrations of titanate greater than 25 μg/mL were avoided to prevent OD from the titanate particles from masking bacterial growth (also assessed by changes in OD). Titanate-bacterial cultures were incubated for 24 h under the conditions appropriate for each type of bacterium. After 24 h, the cultures were thoroughly mixed prior to reading the OD. Control cultures for experiments included cultures of media alone (no titanates or bacteria), titanates in media (no bacteria), and bacteria alone (no titanates). Additional control for bacteriostatic effect included bacteria with erythromycin (100 μg/mL, no titanates), which is an effective antibiotic against many oral pathogens. All experiments were repeated in triplicate to assure reproducibility.

TABLE 2

Metal compounds and titanate loading.

| Metal Ion | Source compound | Supplier | Titanate Loading Concentration (μM) | Loaded Concentration (g metal/g APT) | Loaded Concentration (g metal/g MST) |
|---|---|---|---|---|---|
| Au(III) | $HAuCl_4 \cdot 3H_2O$ | Sigma-Aldrich | 13,251 | 0.0852 | 0.0789 |
| Pd(II) | $PdCl_2$ | Johnson Mathey, Inc. | 13,240 | 0.0539 | 0.0557 |
| Pt(II) | $PtCl_2$ | Johnson Mathey, Inc. | 114 | 0.00086 | 0.00084 |
| Pt(IV) | $PtCl_2$ | Johnson Mathey, Inc. | 14,912 | 0.0155 | 0.0686 |

The initial and final mean and standard deviation OD readings were plotted as a function of concentration. The titanate only controls were also plotted as a baseline. Cultures were statistically compared (two-sided Student's t-tests, $\alpha$=0.05) to determine significant effects of the titanates (with or without added metal) on bacterial growth.

A similar strategy was used to assess the antibacterial action of the metal ions alone, so that the relative efficacy of the titanates alone and titanate metal complexes could be compared to the metal ions alone. The delivery potential of metal ion from the titanate-metal complexes was determined by calculating the total metal mass complexed with the titanates at each titanate particle concentration. This delivery potential was compared with results from metal ions alone. In this manner we were able to establish if the titanate-metal complexes facilitated delivery of metal ions to the bacteria to inhibit growth.

Results

Antibacterial Effects of Metal Ions Alone

Metal ions differed in their ability to suppress planktonic bacterial growth of the species in Table 1. For example, An growth (FIG. 1) was not suppressed by Pt(IV) concentrations ≤750 μM, was suppressed approximately 30% by Pd(II) >1000 μM, and was completely suppressed by Au(III)>10 μM. We could not measure the effects of Pt(II) alone because of limited aqueous solubility of the chloride salt (Table 2); maximum concentrations of the other metal ions were limited by the aqueous solubility of their salts as well. The maximum concentrations achievable in the bacterial cultures was 5-10% of the stock metal ion solutions in Table 1 to maintain the osmolarity, pH, and nutrition of the culture medium when the metal ions were added. A summary of the effects of metal ions alone is listed in Table 3.

In general, the bacteria in Table 1 were equally susceptible to the metal ions alone. Among the metal ions (excepting Pt(II)), Au(III) was the most potent, inhibiting growth of Aa, An, Fn, and Pg by at least 50% above 10-50 μM (Table 3). Yet concentrations of Au(III)≤1500 μM had no observable effect on Pi, which demonstrated the specificity of these effects on bacterial species.

Antibacterial Effects of Titanates (MST and APT) Alone

Figure 2:
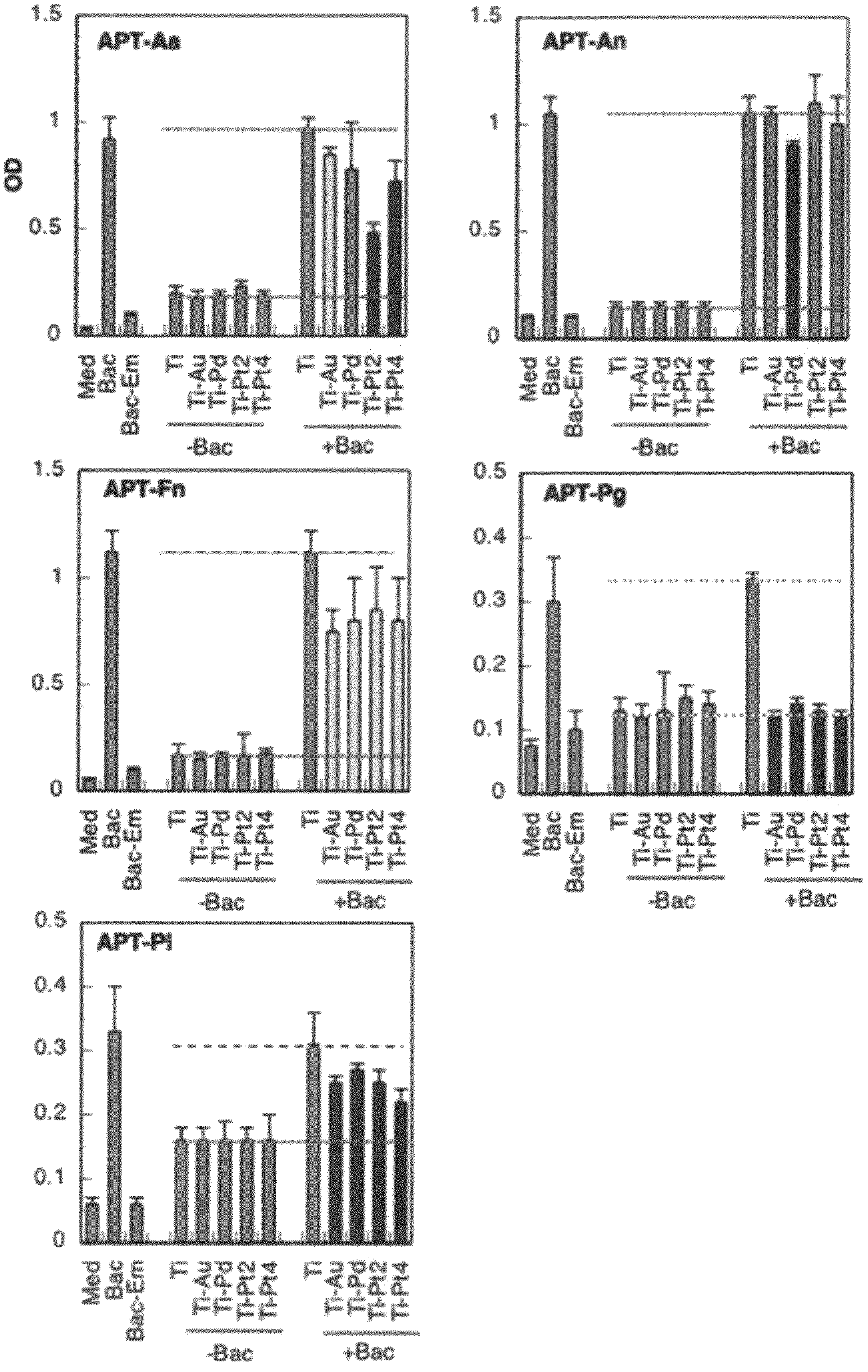
FIG. 2 are dose response curves setting forth the effect of APT compounds loaded with the various metals and the effect on the growth rate of bacteria listed in Table 2.

MST and APT in their sodium forms did not inhibit growth of any of the bacterial species as shown in Table 1 and FIGS. 2 and 3. Growth of the bacterial control cultures varied somewhat by species although approximately equal starting numbers were used (FIGS. 2,3); Pg was the slowest growing of the bacteria tested (Table 1). For all species, the OD values of bacteria alone at 24 h were sufficient (0.3 to 1.2) to detect any inhibition by the titanates. Controls for medium alone (Med) and bacterial with erythromycin (Bac-Em) behaved as expected (FIGS. 2,3). Controls with titanates (no bacteria) had ODs of 0.1-0.15; thus the OD of the titanates did not obscure growth in experiments measuring the effects of loaded or unloaded titanates on bacterial growth.

Antibacterial Effects of Metal-MST or Metal-APT Compounds

The APT or MST loaded with Au(III), Pd(II), Pt(IV), or Pt(II) inhibited growth of some, but not all bacterial species. Bacterial growth suppression varied by metal ion, the type of titanate and the species (FIGS. 2,3). In general, Pi and Pg growth was most susceptible to the metal-titanates, and An was the least susceptible. Among the metal ions tested, Au(III)-titanates most often inhibited growth. However, there were many exceptions and variations. The degree of growth inhibition also varied significantly. As with the titanates alone, control cultures with the metal-titanate compounds added (without bacteria) had OD values of 0.1-0.2. OD among the different metal-titanate compounds and titanates alone did not vary, and the window of OD between maximal bacterial growth and the OD of the metal-titanate compounds ranged from 0.3 to 0.9, providing a sufficient signal range to see any growth inhibition caused by the metal-titanate compounds. Variation among replicates in these tests were generally 10-15%, but sometimes greater (e.g., APT-Fn, FIG. 2).

Protocols were established to assess if titanates could enhance inhibition of bacterial growth by metal ions. Analysis of this enhancement was restricted to conditions where the metal-titanate compounds inhibited bacterial growth by ≥50% (Table 3). For example, 750 μM of Pt(IV) alone did not inhibit Pi growth by 50%, yet the Pt(IV)-APT compound, with a maximum potential delivery of only 2 μM, inhibited Pi growth by 60%. Because APT by itself did not suppress Pi growth, APT appeared to have increased the ability of Pt(IV) to inhibit growth by over 375-fold. Such 'enhancement' appeared to be most common with Pg and Pi. Enhanced effects of Au(III) was common but less (0.9- to 25-fold). Pt(II) was excluded from this analysis because Pt(II) could not be tested by itself in bacterial culture.

The bacteria evaluated in the study are all associated with periodontal disease or dental caries. It is believed that use of the titanate-mediated biodelivery system allows for an effective treatment of periodontal disease or dental caries. For instance, periodontal pockets associated with diseased gums could have an effective amount of the titanate-metal ion delivered to the pocket. Suitable delivery mechanisms may involve direct injection of a solution or ointment containing the titanate/metal ion complex. Other delivery mechanisms used to treat periodontal disease or dental caries may also be employed including the incorporation of the titanate/metal ion complex into various pastes, creams, salves, oral rinses, and similar products.

The current results show unequivocally that metal-titanate compounds inhibit planktonic bacterial growth and that titanates enhance the ability of metal ions to inhibit growth, depending on specific experimental conditions. In spite of these findings, there were few patterns to these effects. Au(III)-MST was the most effective inhibitor of the metal titanates, perhaps reflecting the potency of Au(III) alone (FIG. 1, Table 3) and the ability to load more Au(III) onto the MST (Table 2). On the other hand, the enhancement of Au(III)-induced inhibition by MST was not as large (5-25 fold) as for other elements such as Pt(IV) (over 375 fold in some cases). Such specificity may ultimately be a therapeutic asset.

How metal-titanate compounds inhibit bacterial growth is not known. However, given the relative size of the titanates (1-10 μm, Ref 1) and most bacteria (<0.2 μm), it seems unlikely that bacteria ingest the titanates. The relatively large size of the titanates, current data, and previous research suggest that inhibition is more likely to occur via some direct contact mechanism; many bacteria might bind with one titanate particle. Inhibition by release of metal ions into the medium seems a remote possibility because the metal-titanate compounds are relatively stable and do not release appreciable metal ions over the 24 h test. Furthermore, the maximum potential concentrations of metal ions from the metal-titanate compounds, even if all metal mass was released, were far below inhibitory doses (Table 3). The direct contact mechanism therefore seems likely, even more so than with mammalian cells, where cellular 'ingestion' of the titanate particles is plausible. The direct contact inhibition hypothesis, if true, suggests that the metal-titanate compounds could be used in solid-phase disinfection schemes.

Pd(II) and Pt(IV) ions are more potent inhibitors of mammalian cells than bacteria. The TC50 concentrations for these ions against the bacteria in Table 1 were >750-1500 μM (Table 3), yet Pd(II) inhibits mammalian cells at 100-300 μM and Pt(IV) at 25 μM based on previous reports. This differential is not encouraging for metal ions for systemic treatment of bacterial infections in human tissues. Yet the metal-titanate compounds inhibited bacterial growth (e.g., Pi and Pg) with far lower metal ion loads (2-13 μM; Table 3). Coupled with the solid phase nature of the titanates to limit systemic distribution, the titanates may provide a favorable shift of the therapeutic index for these metal ions as antibacterials. For Au(III), these factors were more favorable because the inhibitory concentration for bacteria (often 10-50 μM, Table 3) was below that for several types of mammalian cells (60-115 μM, Ref 10), and titanates inhibited bacteria at effective doses of 0.4-11 μM (Table 3). For Pt(II), the solubility of the ion alone was so low that its toxicity could not even be tested, yet Pt(II)-APT was an effective inhibitor of Aa and Pg growth at doses of only 0.11 μM (Table 3). All of these data suggest a therapeutic advantage of the metal-titanate compounds as antibacterials.

If safe and effective metal-titanate bacterial inhibitors could be developed, several therapeutic roles come to mind. Intraorally, metal-titanates could be used as an adjunct treatment at the base of carious lesions, in residual canals post-endodontic therapy, or incorporated into restorative materials to limit recurrent caries at the margins of restorations. Titanates could be used in any poorly perfused area to inhibit bacterial growth where the solid-phase would be advantageous; one example would be in osteomyelitis. On the skin, titanates might be used in bandages to limit bacterial growth in wounds or ingress into wounds.

In spite of potential for therapy, significant barriers remain to clinical utility. The current results do not reveal if bacterial growth inhibition results from bacterial killing. The compounds may only suppress growth. Current results are limited to planktonic assays, yet most tissue infections occur in an organized biofilm. And current results are limited by relatively low loading levels of the titanates (Table 1); other particle sizes or loading strategies might boost the potential to deliver metal ions or change mechanisms of inhibition.

In conclusion, the current results show that by themselves, sodium titanates (MST or APT) have no effect on planktonic growth of several oral bacterial species, but that inhibition of growth is possible when Au(III), Pd(II), Pt(II), or Pt(IV) are loaded onto the MST or APT. Furthermore, the current results support a facilitative role for the titanates in metal-mediated inhibition of bacterial growth in some cases.

TABLE 3

Suppression of bacterial growth by metal ions and metal-titanate compounds.

| | | TC50 | MST-metal compound | | | | APT-metal compound | | | |
|---|---|---|---|---|---|---|---|---|---|---|
| Bacteria | Metal Ion | Conc., Metal ion Alone (μM)* | Max. Bacterial Growth Suppression (%) | Inhibitory Conc. (μg/mL)** | Max. Metal ion Delivery (μM)*** | Titanate Enhancement of Metal Suppression (fold)**** | Max. Bacterial Growth Suppression (%) | Inhibitory Conc. (μg/mL)** | Max. Metal ion Delivery (μM)*** | Titanate Enhancement of Metal Suppression (fold)**** |
| Aa | Au(III) | 10 | 100# | 5# | 2 | 5 | 10 | 25 | — | — |
| | Pd(II) | 1500 | 0 | — | — | — | 25 | 10 | — | — |
| | Pt(II) | ND@ | 0 | — | — | — | 60# | 25# | 0.11 | — |
| | Pt(IV) | >1500 | 20 | 25 | — | — | 30# | 25# | — | — |

TABLE 3-continued

Suppression of bacterial growth by metal ions and metal-titanate compounds.

| | | TC50 | MST-metal compound | | | | APT-metal compound | | | |
|---|---|---|---|---|---|---|---|---|---|---|
| Bacteria | Metal Ion | Conc., Metal ion Alone (μM)* | Max. Bacterial Growth Suppression (%) | Inhibitory Conc. (μg/mL)** | Max. Metal ion Delivery (μM)*** | Titanate Enhancement of Metal Suppression (fold)**** | Max. Bacterial Growth Suppression (%) | Inhibitory Conc. (μg/mL)** | Max. Metal ion Delivery (μM)*** | Titanate Enhancement of Metal Suppression (fold)**** |
| An | Au(III) | 50 | 80[#] | 20[#] | 8 | 6 | 0 | — | — | — |
| | Pd(II) | >1500 | 10 | 25 | — | — | 10[#] | 10[#] | — | — |
| | Pt(II) | ND | 0 | — | — | — | 0 | — | — | — |
| | Pt(IV) | >750 | 0 | — | — | — | 0 | — | — | — |
| Fn | Au(III) | 10 | 100[#] | 5[#] | 2 | 5 | 40 | 25 | — | — |
| | Pd(II) | 1000 | 0 | — | — | — | 30 | 10 | — | — |
| | Pt(II) | ND | 0 | — | — | — | 25 | 25 | — | — |
| | Pt(IV) | 750 | 0 | — | — | — | 35 | 10 | — | — |
| Pg | Au(III) | 10 | 100[#] | 1[#] | 0.4 | 25 | 100[#] | 25[#] | 11 | 0.9 |
| | Pd(II) | >1500 | 45[#] | 25[#] | — | — | 100[#] | 25[#] | 13 | >190 |
| | Pt(II) | ND | 20 | 25 | — | — | 100[#] | 25[#] | — | — |
| | Pt(IV) | >750 | 40[#] | 25[#] | — | — | 100[#] | 25[#] | 2 | >375 |
| Pi | Au(III) | >1500 | 30[#] | 25[#] | — | — | 30[#] | 25[#] | | — |
| | Pd(II) | 1500 | 60[#] | 25[#] | 13 | 115 | 15[#] | 25[#] | | — |
| | Pt(II) | ND | 30[#] | 25[#] | — | — | 30[#] | 10[#] | | — |
| | Pt(IV) | >750 | 60[#] | 10[#] | 3.5 | >210 | 60[#] | 25[#] | 2 | >375 |

Red cells indicate that bacterial growth suppression was ≥50% vs. titanate controls. Green indicates that titanates enhanced metal interactions with bacteria.

*Concentration that suppressed bacterial growth by ≥50% vs control

**Concentration of loaded metal-titanate compound that suppressed bacterial growth maximally relative to titanate-only controls.

***Assuming that all of the loaded metal was delivered to the bacteria from the inhibitory metal-titanate concentration.

*****TC50 concentration of ion alone to divided by the maximal delivered concentration when titanate-compound suppressed bacterial growth by ≥50% vs. controls.

[#]Statistical significance vs. titanate-only controls (paired t-test, $\alpha = 0.05$).

[@]Not done. Concentration of Pt(II) solution not high enough for cell-culture experiments at high Pt(II) concentrations.

— Not calculated because conditions for accurate calculations not met or data not available.

Additional details directed to protocols, the nature of the methods, and results may be seen in reference to Applicant's publication entitled "Peroxotitanate- and Monosodium Metal-type Tinate Compound as Inhibitors of Bacterial Growth", The Journal of Biomedical Materials Research, June 2011, Volume 97A, issue 3 and which is incorporated herein by reference.

The data indicates that various types of organisms may respond differently to various ions as well as to the titanate used to deliver the ion. However, in the cases noted above, the reduction in the organism growth and viability was observed at metal ion levels at least one order of magnitude less than a metal ion typically needed to bring about similar antimicrobial activity where titanates are not utilized.

While the side effects of various metal ions used to suppress bacterial growth are well known, such effects are dose dependent and are greatly reduced or not apparent at low metal ion concentrations. The ability to provide metal ions capable of suppressing bacterial growth at one or more orders of magnitude lower concentration than required for metal ions significantly expands treatment options and therapeutic strategies of using metal ions to treat bacterial infections.

The data set forth herein used maximum loading capabilities of titanate-metal ions for which the positive reduction of bacterial growth is noted. The exact dosage requirements that maybe needed to bring about a desired therapeutic effect maybe established by routine screening and evaluation and is well within the ordinary skill level of one in the art.

It is further envisioned that use of the titanate-metal ion delivery system can be used with any number of site specific medical delivery systems so as to target a metal ion to a specific organ or region of the body. For instance, various monoclonal or polyclonal antibodies could possibly be conjugated to the titanate-metal ion complex so as to deliver the complex to a targeted region. Other well known targeting systems including various ligands, lectins or chemical carriers may be utilized as well as various mechanical delivery systems for targeting delivery of a therapeutic region to a specified location or region.

It is believed that any metal ion having an ability to suppress bacterial growth may be utilized with the titanate delivery system described herein. Through routine experimentation one of ordinary skill in the art and readily determine if the titanate delivery system has a beneficial synergistic effect with respect to the metal ion and the bacterium of interest such that the synergistic properties of the titanate-metal ion complex are achieved.

Further, it is believed that metal-loaded titanates can be incorporated into traditional medical ointments, bandages, implantable biomaterials, coatings on invasive apparatuses such as catheters, shunts, and similar devices to prevent or limit bacterial infections. The metal-loaded titanates are believed to be compatible with traditional antibiotic ointments and creams. Metal-loaded titanate may also be incorporated as coatings on surgical suture material to help suppress growth and/or formation of bacterial infections.

Although preferred embodiments of the invention have been described using specific terms, devices, and methods, such description is for illustrative purposes only. The words used are words of description rather than of limitation. It is to be understood that changes and variations may be made by those of ordinary skill in the art without departing from the spirit or the scope of the present invention which is set forth in the following claims. In addition, it should be understood that aspects of the various embodiments may be interchanged, both in whole, and in part. Therefore, the spirit and scope of the appended claims should not be limited to the description of the preferred versions contained therein.

That which is claimed:

1. A process for treating oral bacteria, said oral bacteria selected from the group consisting of *Porphyromonas gingivalis, Fusobacterium nucleatum, Agregatibacter actinomycetemcomitans, Streptoccoccus mutans, Prevotella intermedia* and *Actinomyces naeslundii;* comprising exposing said bacteria to a pharmaceutical composition comprising a metal ion and a titanate carrier molecule bound to said metal ion, said titanate carrier molecule is selected from the group consisting of monosodium titanate, amorphous peroxotitanate, and combination thereof;

wherein said pharmaceutical composition provides an antibiotic effect on said bacteria.

2. A process for treating oral bacteria, said oral bacteria selected from the group consisting of *Porphyromonas gingivalis, Fusobacterium nucleatum, Agregatibacter actinomycetemcomitans, Streptoccoccus mutans, Prevotella intermedia* and *Actinomyces naeslundii;* comprising exposing said bacteria to a pharmaceutical composition comprising a metal ion and a titanate carrier molecule bound to said metal ion in a concentration range from about 1 mg/L to about 25 mg/L, said titanate carrier molecule is selected from the group consisting of monosodium titanate, amorphous peroxotitanate, and combination thereof;

wherein said pharmaceutical composition provides an antibiotic effect on said bacteria.

3. A process for treating oral bacteria, said oral bacteria selected from the group consisting of *Porphyromonas gingivalis, Fusobacterium nucleatum, Agregatibacter actinomycetemcomitans, Streptoccoccus mutans, Prevotella intermedia* and *Actinomyces naeslundii;* comprising exposing said bacteria to a pharmaceutical composition comprising a metal ion selected from a group consisting of Au(III), Pd(II), Pt(II), Pt(IV) and combinations thereof, and a titanate carrier molecule bound to, said metal ion, said titanate carrier molecule is selected from the group consisting of monosodium titanate, amorphous peroxotitanate, and combination thereof;

wherein said pharmaceutical composition provides an antibiotic effect on said bacteria.

4. The process according to claim 2 wherein said metal ion is selected from the group consisting of Au(III), Pd(II), Pt(II), Pt(IV) and combinations thereof.

5. The process according to claim 1 wherein said pharmaceutical composition is one of a mouthwash, a toothpaste, an oral rinse, or an oral gel.

6. The process according to claim 2 wherein said pharmaceutical composition is one of a mouthwash, a toothpaste, an oral rinse, or an oral gel.

7. The process according to claim 3 wherein said pharmaceutical composition is one of a mouthwash, a toothpaste, an oral rinse, or an oral gel.

* * * * *

UNITED STATES PATENT AND TRADEMARK OFFICE

CERTIFICATE OF CORRECTION

PATENT NO. : 8,545,820 B2
APPLICATION NO. : 13/135745
DATED : October 1, 2013
INVENTOR(S) : David T. Hobbs et al.

It is certified that error appears in the above-identified patent and that said Letters Patent is hereby corrected as shown below:

In the Specification

| | |
|---|---|
| Column 1, Line 15: | This invention was made with Government support under Contract No. DE-AC09-08SR22470 awarded by the United States Department of Energy. The Government has certain rights in the invention. |
| Should read: | This invention was made with Government support under Grant No. R01 DE021373 awarded by the National Institutes of Health, and Contract No. DE-AC09-08SR22470 awarded by the United States Department of Energy. The Government has certain rights in the invention. |

Signed and Sealed this
Twenty-third Day of March, 2021

Drew Hirshfeld
*Performing the Functions and Duties of the*
*Under Secretary of Commerce for Intellectual Property and*
*Director of the United States Patent and Trademark Office*